(12) United States Patent
Bratkovski et al.

(10) Patent No.: US 8,223,331 B2
(45) Date of Patent: Jul. 17, 2012

(54) SIGNAL-AMPLIFICATION DEVICE FOR SURFACE ENHANCED RAMAN SPECTROSCOPY

(75) Inventors: Alexandre M. Bratkovski, Mountain View, CA (US); Theodore I. Kamins, Palo Alto, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 474 days.

(21) Appl. No.: 12/487,940

(22) Filed: Jun. 19, 2009

(65) Prior Publication Data

US 2010/0321684 A1    Dec. 23, 2010

(51) Int. Cl.
*G01J 3/44* (2006.01)
(52) U.S. Cl. .................................................. 356/301
(58) Field of Classification Search ............ 356/301, 356/244–246
See application file for complete search history.

(56) References Cited

U.S. PATENT DOCUMENTS

| | | | | |
|---|---|---|---|---|
| 4,448,485 A | * | 5/1984 | Bergman et al. | 359/328 |
| 2004/0023046 A1 | * | 2/2004 | Schlottig et al. | 428/469 |
| 2006/0057360 A1 | * | 3/2006 | Samuelson et al. | 428/323 |
| 2006/0215154 A1 | * | 9/2006 | Chan et al. | 356/244 |
| 2006/0225162 A1 | * | 10/2006 | Yi | 977/754 |
| 2007/0224104 A1 | * | 9/2007 | Kim | 423/445 B |
| 2008/0079104 A1 | * | 4/2008 | Stewart et al. | 257/433 |
| 2008/0081388 A1 | * | 4/2008 | Yasseri et al. | 438/22 |
| 2009/0279085 A1 | * | 11/2009 | Ebstein | 356/301 |

OTHER PUBLICATIONS

Talian et al., "Surface-enhanced Raman spectroscopy on novel black silicon-based nanostructured surfaces", Jan. 2009, Journal of Raman Spectroscopy, pp. 1-5.*

* cited by examiner

*Primary Examiner* — Kara E Geisel

(57) ABSTRACT

A signal-amplification device for surface enhanced Raman spectroscopy (SERS). The signal-amplification device includes a non-SERS-active (NSA) substrate, a plurality of multi-tiered non-SERS-active nanowire (MNSANW) structures and a plurality of metallic SERS-active nanoparticles. In addition, a MNSANW structure of the plurality of MNSANW structures includes a main arm of a plurality of main arms and a plurality of arms of at least secondary order. The plurality of main arms is disposed on the NSA substrate; and, a secondary arm of the plurality of arms is disposed on the main arm. Moreover, a metallic SERS-active nanoparticle of the plurality of metallic SERS-active nanoparticles is disposed on a surface of the MNSANW structure.

19 Claims, 15 Drawing Sheets

700

REPEAT 610 AND 620 AT LEAST ONE TIME TO PRODUCE A PLURALITY
OF SUBORDINATE ARMS ON THE MNSANW STRUCTURE
710

FIG. 7

SIGNAL-AMPLIFICATION DEVICE FOR SURFACE ENHANCED RAMAN SPECTROSCOPY

TECHNICAL FIELD

Embodiments of the present invention relate to Raman spectroscopy.

BACKGROUND

Raman spectroscopy has emerged as a leading technique for the analysis of the structure of inorganic materials and complex organic molecules. Scientists engaged in the application of Raman spectroscopy have found that by decorating a surface, upon which a molecule is later adsorbed, with a thin layer of a metal in which surface plasmons have frequencies in a range of electromagnetic radiation used to excite such a molecule and in which surface plasmons have frequencies in a range of electromagnetic radiation emitted by such a molecule, it is possible to enhance the intensity of a Raman spectrum of such a molecule. This technique has been termed surface enhanced Raman spectroscopy (SERS).

In addition, spectroscopists utilizing spectroscopic techniques for the analysis of molecular structures have a continuing interest in improving the sensitivity of their spectroscopic techniques. Not only is improved sensitivity desirable for reducing the time of analysis, but also improved sensitivity can provide previously unachievable results. For example, improved sensitivity is directly related to lower detectability limits for previously undetected molecular constituents. Thus, scientists engaged in the application of Raman spectroscopy are motivated to improve the sensitivity of SERS for the detection of molecules and the spectral signatures of moieties in these molecules.

DESCRIPTION OF THE DRAWINGS

The accompanying drawings, which are incorporated in and form a part of this specification, illustrate embodiments of the invention and, together with the description, serve to explain the embodiments of the invention:

FIG. 7 is a flow chart of yet further embodiments of the method of FIG. 6 for fabricating the signal-amplification device for SERS, in an embodiment of the present invention.

The drawings referred to in this description should not be understood as being drawn to scale except if specifically noted.

DESCRIPTION OF EMBODIMENTS

Reference will now be made in detail to the alternative embodiments of the present invention. While the invention will be described in conjunction with the alternative embodiments, it will be understood that they are not intended to limit the invention to these embodiments. On the contrary, the invention is intended to cover alternatives, modifications and equivalents, which may be included within the spirit and scope of the invention as defined by the appended claims.

Furthermore, in the following description of embodiments of the present invention, numerous specific details are set forth in order to provide a thorough understanding of the present invention. However, it should be noted that embodiments of the present invention may be practiced without these specific details. In other instances, well known methods, procedures, and components have not been described in detail as not to unnecessarily obscure embodiments of the present invention.

Embodiments of the present invention include a signal-amplification device for surface enhanced Raman spectroscopy (SERS). The signal-amplification device includes a non-SERS-active (NSA) substrate, a plurality of multi-tiered non-SERS-active nanowire (MNSANW) structures, and a plurality of metallic SERS-active nanoparticles. In addition, a MNSANW structure of the plurality of MNSANW structures includes a main arm of a plurality of main arms and a plurality of arms of at least secondary order. The plurality of main arms is disposed on the NSA substrate; and, a secondary arm of the plurality of arms is disposed on the main arm. Moreover, a metallic SERS-active nanoparticle of the plurality of metallic SERS-active nanoparticles is disposed on a surface of the MNSANW structure. As used herein, the term of art "tier" refers to an order of arms of a multi-tiered non-SERS-active nanowire structure, as is subsequently described in greater detail. Also, as used herein, the term of art "SERS-active" means that the described "SERS-active" entity participates in the surface enhancement effect of SERS; on the other hand, "non-SERS-active" means that the described "non-SERS-active" entity does not participate in the surface enhancement effect of SERS.

Figure 1A:
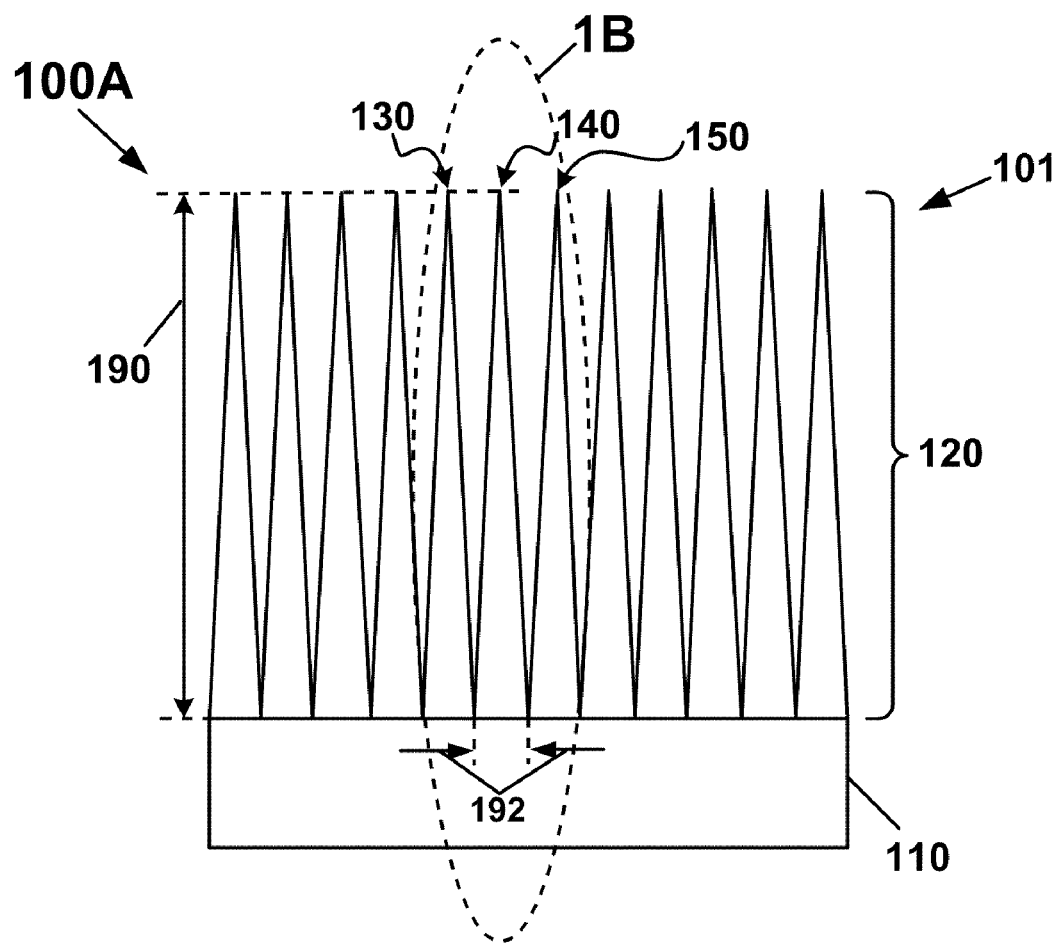
FIG. 1A is a cross-sectional elevation view of a signal-amplification device for surface enhanced Raman spectroscopy (SERS) illustrating the configuration of a plurality of main arms of a plurality of multi-tiered non-SERS-active nanowire (MNSANW) structures on a non-SERS-active (NSA) substrate of the signal-amplification device, in an embodiment of the present invention.

With reference now to FIG. 1A, in accordance with embodiments of the present invention, a cross-sectional elevation view 100A of a signal-amplification device 101 for SERS is shown. FIG. 1A shows the configuration of a plurality of main arms of a plurality 120 of MNSANW structures, for example, MNSANW structures 130, 140 and 150, on a substrate, for example, a NSA substrate 110, of the signal-amplification device 101. As shown in FIG. 1A, the plurality 120 of MNSANW structures, for example, MNSANW structures 130, 140 and 150, are shown without arms of higher order than the order of a main arm to emphasize the configuration of the main arms on the substrate. Thus, the plurality 120 of MNSANW structures, for example, MNSANW structures 130, 140, and 150, are shown as the plurality of main arms of the plurality 120 of MNSANW structures. A main arm of the plurality of main arms may have, by way of example without limitation thereto, an aspect ratio of about 10 to 1 as indicated by the ratio of a height 190 to a width 192 of the base of the main arm, for example, the main arm of MNSANW structure 140. The width 192 of the base of the main arm, for example, the main arm of MNSANW structure 140, may have a nominal width of about 1 micrometer (μm); and, the height 190 of a main arm, for example the main arm of MNSANW structure 140, may be between about 5 μm and 20 μm. As shown in FIG. 1A, the plurality of main arms disposed on the NSA substrate 110 may include black silicon. The NSA substrate 110 may include, by way of example without limitation thereto, silicon. However, in other embodiments of the present invention, the NSA substrate 110 also includes other materials which are also not SERS active, in the sense that they do not produce surface enhancement in Raman spectroscopy, for example, germanium, silicon-germanium, other non-metals and even selected metals, which do not exhibit the surface enhancement effect in Raman spectroscopy. "Black silicon" is a term of art for a structure on the surface of a silicon substrate that has been etched to produce a plurality of asperities on the surface of the silicon substrate, which is cone-like, columnar or brush-like and traps light. Alternatively, in other embodiments of the present invention, any cone-like, columnar or brush-like, light-trapping structure might be used instead of black silicon. Black silicon may be produced by etching with aqueous solutions, such as those containing potassium hydroxide, or alternatively, by any of a variety of dry etching techniques, such as plasma etching, or reactive ion etching with suitable excited neutral and ionized species, for example, fluorine bearing compounds, such as sulfur hexafluoride ($SF_6$), with a moderating or passivating agent, such as octafluorocyclobutane ($C_4F_8$) or trifluoromethane ($CHF_3$). In circle 1B, a few MNSANW structures, for example, MNSANW structures 130, 140 and 150, are shown disposed on the NSA substrate 110, which are next described in greater detail.

Figure 1B:
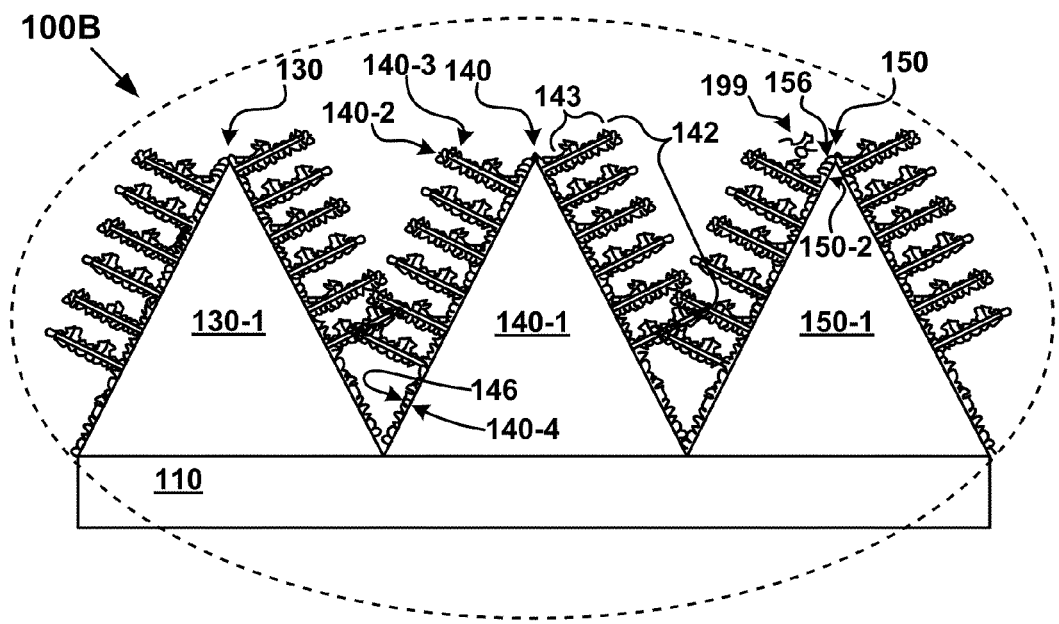
FIG. 1B is an enlarged cross-sectional elevation view of encircled portion 1B of the signal-amplification device of FIG. 1A detailing the configuration of a plurality of arms of higher order on the plurality of MNSANW structures of the signal-amplification device and of a molecule disposed in proximity to a plurality of metallic SERS-active nanoparticles configured to enhance a Raman spectrum of the molecule, in an embodiment of the present invention.

With reference now to FIG. 1B, in accordance with embodiments of the present invention, an enlarged cross-sectional elevation view 100B of encircled portion 1B of the signal-amplification device 101 of FIG. 1A is shown. The encircled portion 1B of the signal-amplification device 101 has been expanded in the direction parallel to the width 192 of the base of the main arm of MNSANW structure 140 so as to show in detail the morphology of the plurality 120 of MNSANW structures, for example, MNSANW structures 130, 140 and 150. FIG. 1B details the configuration of a plurality of arms of higher order, for example, secondary arm 140-2, on the plurality 120 of MNSANW structures of the signal-amplification device 101, of which MNSANW structure 140 is an example, and of a molecule 199 that is disposed in proximity to a plurality of metallic SERS-active nanoparticles that are configured to enhance a Raman spectrum of the molecule 199, of which metallic SERS-active nanoparticle 156 is an example. The signal-amplification device 101 for SERS includes the NSA substrate 110, a plurality of MNSANW structures, for example, MNSANW structures 130, 140 and 150, and a plurality of metallic SERS-active nanoparticles, for example, metallic SERS-active nanoparticle 146 and metallic SERS-active nanoparticle 156. The plurality of MNSANW structures includes a main arm, for example, main arm 140-1, of a plurality of main arms, for example, main arms 130-1, 140-1 and 150-1, and a plurality, for example, plurality 142, of arms of at least secondary order. The plurality of main arms, for example, main arms 130-1, 140-1 and 150-1, is disposed on the NSA substrate 110. Secondary arm 140-2 of the plurality 142 of arms of at least secondary order is disposed on the main arm 140-1. A metallic SERS-active nanoparticle 146 of the plurality of metallic SERS-active nanoparticles is disposed on a surface 140-4 of the MNSANW structure 140, which includes the surfaces of arms of all orders of MNSANW structure 140. As shown in FIG. 1B, the plurality of metallic SERS-active nanoparticles is shown as being distributed over the entire surface of the plurality 120 of MNSANW structures, for example, MNSANW structures 130, 140 and 150; for example, the metallic SERS-active nanoparticle 156 is also shown as being disposed on a surface 150-2 of the MNSANW structure 150, which includes the surfaces of arms of all orders of MNSANW structure 150.

With further reference to FIG. 1B, in accordance with embodiments of the present invention, the MNSANW structure 140 of the plurality 120 of MNSANW structures of the signal-amplification device 101 may also include a plurality 143 of subordinate arms, of which tertiary arm 140-3 is an example. A subordinate arm of the plurality 143 of subordinate arms may be selected from the group consisting of tertiary arms, quaternary arms and arms of higher order than quaternary. A subordinate arm of the plurality of subordinate arms is disposed on an arm of lower order than an order of the subordinate arm. As used herein, the term of art "higher order" means an arm designated by an ordinal descriptor greater than an ordinal descriptor of a given arm. For example, a secondary arm is of higher order than the order of a main, or primary, arm, because the ordinal descriptor "secondary" designates the ordinal number two which is greater than the ordinal number one, which is defined herein as the ordinal number of the main arm; a tertiary arm is of higher order than the order of a secondary arm, because the ordinal descriptor "tertiary" designates the ordinal number three which is greater than the ordinal number two and the ordinal number one, which are the ordinal numbers of a secondary arm and a main arm, respectively. Similarly, a quaternary arm is of higher order than the order of a tertiary arm, a secondary arm and main arm, because the ordinal descriptor "quaternary" designates the ordinal number four which is greater than the ordinal numbers three, two and one, which are the ordinal numbers of a tertiary arm, a secondary arm and a main arm, respectively. Also, as used herein, the term of art "lower order" means an arm designated by an ordinal descriptor lower than an ordinal descriptor of a given arm. For example, a main arm is of lower order than the order of a secondary arm, because the description "main" as used herein, defines the ordinal number of the main arm, the ordinal number one, which is less than the ordinal number two, which is the ordinal number of a secondary arm; a secondary arm is of lower order than the order of a tertiary arm, because the ordinal descriptor "secondary" designates the ordinal number two which is less than the ordinal number three, which is the ordinal number of a tertiary arm. Similarly, a tertiary arm is of lower order than the order of a quaternary arm, because the ordinal descriptor "tertiary" designates the ordinal number three which is less than the ordinal number four, which is the ordinal numbers of a quaternary arm. Thus, as shown in FIG. 1B, in one embodiment of the present invention, tertiary arm 140-3 of the MNSANW structure 140 is disposed on the secondary arm 140-2, which is an arm of lower order than the order of tertiary arm 140-3. Alternatively, in another embodiment of the present invention, a tertiary arm of the MNSANW structure 140 may be disposed on the main arm 140-1, which is also an arm of lower order than the order of a tertiary arm. Moreover, as used herein, the term of art "tier" refers to an order of arms of a MNSANW structure. For example, the main arms are a first tier of arms; the secondary arms are a second tier of arms; the tertiary arms are a third tier of arms; and, the quaternary arms are a fourth tier of arms. Thus, the term of art "multi-tiered" refers to a MNSANW structure including more than a first tier of arms.

With further reference to FIG. 1B, in accordance with embodiments of the present invention, at least one metallic SERS-active nanoparticle, for example, metallic SERS-active nanoparticle 156, of the plurality of metallic SERS-active nanoparticles is configured to enhance the Raman spectrum of the molecule 199 disposed in proximity to the metallic SERS-active nanoparticle 156. In one embodiment of the present invention, the metallic SERS-active nanoparticle 156 of the plurality of metallic SERS-active nanoparticles may be composed of a noble metal constituent. In another embodiment of the present invention, the metallic SERS-active nanoparticle 156 of the plurality of metallic SERS-active nanoparticles may be composed of a constituent selected from the group of constituents consisting of copper, silver, gold, aluminum, tungsten, palladium, platinum and mercury.

Figure 2A:
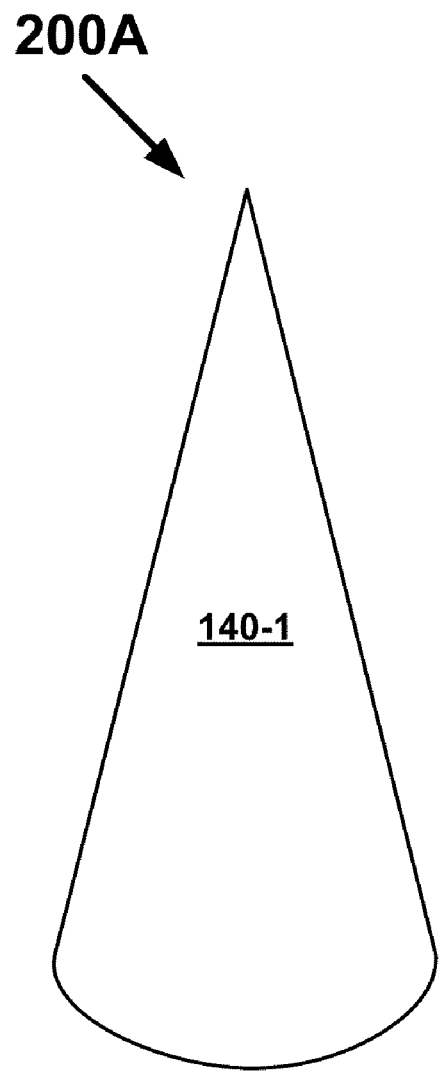
FIG. 2A is a perspective view of the main arm of a MNSANW structure of the signal-amplification device of FIGS. 1A and 1B illustrating the surface morphology of the main arm after etching the NSA substrate to produce the plurality of main arms for the plurality of MNSANW structures, in an embodiment of the present invention.

With reference now to FIG. 2A, in accordance with embodiments of the present invention, a perspective view 200A of the main arm 140-1 of MNSANW structure 140 of the signal-amplification device 101 of FIGS. 1A and 1B is shown. FIG. 2A shows the surface morphology of the main arm 140-1 after etching the NSA substrate 110 to produce the plurality of main arms, for example, main arms 130-1, 140-1 and 150-1, for the plurality 120 of MNSANW structures, for example, MNSANW structures 130, 140 and 150. As shown in FIG. 2A, at least one main arm 140-1 of the plurality of main arms, for example, main arms 130-1, 140-1 and 150-1, of the signal-amplification device 101 has a substantially conical shape, by way of example without limitation thereto. As used herein, the term of art "substantially conical shape" means that a shape of a main arm, for example, main arm 140, is that of a solid that has an apex, a base and an approximately rounded, or approximately polygonal, periphery of a section through the solid that is taken perpendicular to a centerline extending from the center of the base to the apex, and of a solid that is such that the surface of the solid may be characterized by an average radius, or average apothem, respectively, of the periphery of the section perpendicular to the centerline of the solid that is generally monotonically decreasing in proceeding from the base to the apex. In another embodiment of the present invention, a main arm of a MNSANW structure may have a shape of a spike; the term of art "spike" means that the main arm is an asperity with an apex and a base. In an embodiment of the present invention, the spike is disposed on the NSA substrate 110. As previously discussed in the description of FIG. 1A, asperities that serve as the main arms of the plurality 120 of MNSANW structures, for example, MNSANW structures 130, 140 and 150, may be provided by a method for fabricating a signal-amplification device 101 for SERS that includes etching a silicon substrate to produce a plurality of main arms for a plurality of MNSANW structures, such as asperities on a NSA substrate 110, as is the case for black silicon.

Figure 2B:
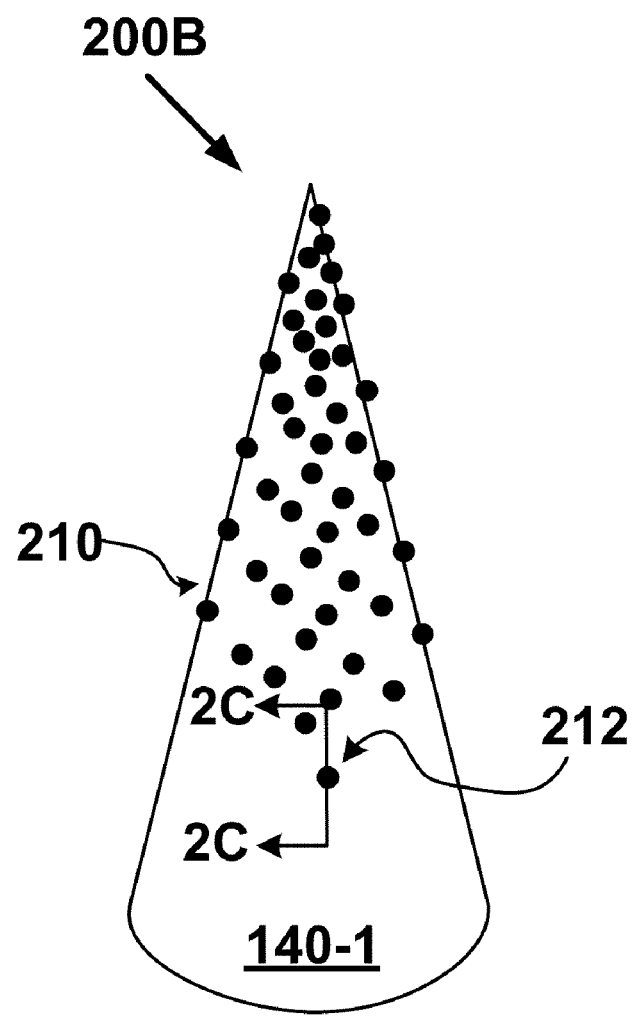
FIG. 2B is a perspective view of the main arm of the MNSANW structure of the signal-amplification device of FIGS. 1A and 1B illustrating a plurality of metallic nanowire (NW)-catalyst seeds disposed on a surface of the main arm, in an embodiment of the present invention.

With reference now to FIG. 2B, in accordance with embodiments of the present invention, a perspective view 200B of the main arm of a MNSANW structure of the signal-amplification device 101 of FIGS. 1A and 1B is shown. FIG. 2B shows a plurality of metallic nanowire(NW)-catalyst seeds, of which metallic NW-catalyst seed 212 is an example, disposed on a surface 210 of main arm 140-1. As shown in FIG. 2B, the plurality of metallic NW-catalyst seeds is shown as a plurality of small rounded specks on the surface 210 of the main arm 140-1, of which metallic NW-catalyst seed 212 is an example. The plurality of metallic NW-catalyst seeds may be provided by the method for fabricating the signal-amplification device 101 for SERS that includes producing the plurality of metallic NW-catalyst seeds disposed on surfaces of the main arms. In embodiments of the present invention, the metal used for the metallic NW-catalyst seeds may be a noble metal, a transition metal or other metal. In one embodiment of the present invention, the metallic NW-catalyst seeds may be produced by physical vapor deposition (PVD) of a thin metallic layer followed by annealing to agglomerate the deposited metallic material into discrete nanoparticles. In another embodiment of the present invention, annealing may be used to also coarsen the metallic NW-catalyst seeds. Alternatively, in another embodiment of the present invention, pre-formed nanoparticles may be deposited on the surface to provide the metallic NW-catalyst seeds. In yet another embodiment of the present invention, the metallic NW-catalyst seeds may be produced by chemical vapor deposition (CVD) using inorganic or metalo-organic (MOCVD) precursors. As an example of a CVD process, nanoparticles of a transition metal, for example, titanium, can be formed using a gaseous precursor containing the transition metal, for example, titanium tetrachloride, which is made to react in a CVD chamber in which the combination of the NSA substrate 110 and the plurality of main arms disposed on the NSA substrate 110, such as black silicon, is placed. Under conditions giving rise to the reaction of the precursor containing the transition metal, the transition metal may be deposited on the surface 210 of the main arm 140-1. The deposited transition metal atoms may then aggregate into the plurality of metallic NW-catalyst seeds disposed on the surfaces of the main arms.

With further reference now to FIG. 2B, in accordance with embodiments of the present invention, the metallic NW-catalyst seeds, of which metallic NW-catalyst seed 212 is an example, may be composed of a constituent selected from the group of constituents consisting of aluminum, silver, gold, platinum, palladium, titanium and nickel. The trace of a plane 2C-2C, which indicates the location of a cross-section through the metallic NW-catalyst seed 212, is also shown in FIG. 2B. These metallic NW-catalyst seeds on the surface of a MNSANW structure provide nuclei for the growth of secondary arms. Although the terms of art "nanoparticle," or "nanoparticles," are used, herein, to describe both metallic NW-catalyst seeds and metallic SERS-active nanoparticles, the function of nanoparticles used as metallic NW-catalyst seeds is different from the metallic SERS-active nanoparticles in that nanoparticles used as metallic NW-catalyst seeds provide a catalyst for the growth of the nanowires. However, it is possible that, after the growth of a nanowire, the remaining nanoparticle used as a metallic NW-catalyst seed for the growth of the nanowire may also provide the function of a metallic SERS-active nanoparticle depending upon the size and composition of the metallic NW-catalyst seed. Such metallic NW-catalyst seeds may also provide nuclei for the growth of subordinate arms of higher order on arms of lower order, which is subsequently described. Embodiments of the present invention by which a secondary arm, for example, secondary arm 140-2, is grown on the main arm, for example, main arm 140-1, are next described.

Figure 2C:
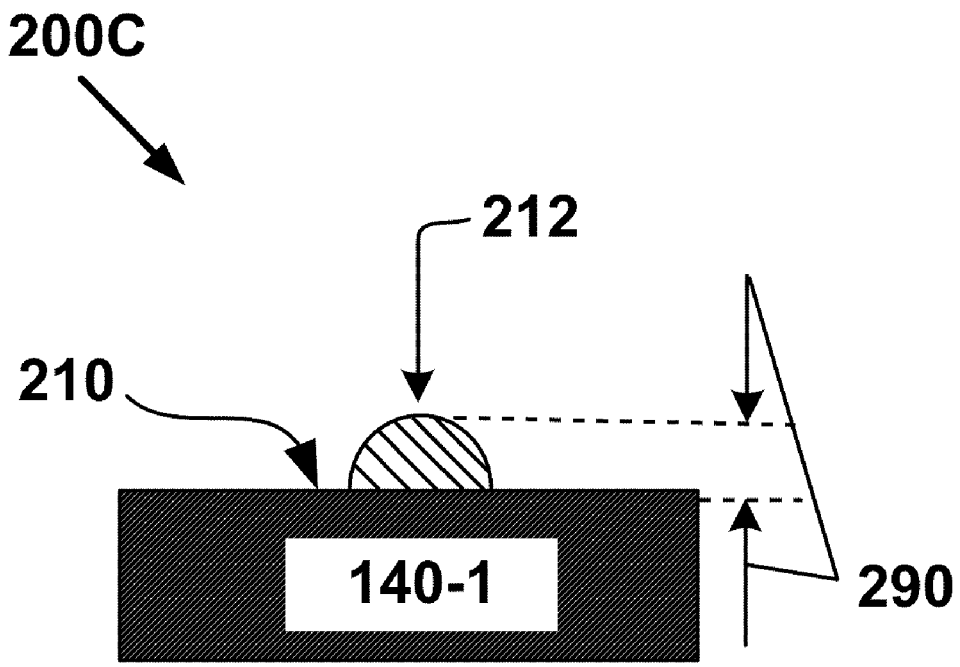
FIG. 2C is a cross-sectional elevation view of a metallic NW-catalyst seed disposed on the surface of the main arm of FIG. 2B illustrating the configuration of the metallic NW-catalyst seed on the main arm prior to growing an arm of higher order than the order of the main arm at a site of the metallic NW-catalyst seed, in an embodiment of the present invention.

With reference now to FIG. 2C, in accordance with embodiments of the present invention, a cross-sectional elevation view 200C of a metallic NW-catalyst seed 212 disposed on the surface 210 of the main arm 140-1 of FIG. 2B is shown. FIG. 2C shows the configuration of the metallic NW-catalyst seed 212 on the main arm 140-1 prior to growing an arm of higher order than the order of the main arm 140-1 at a site of the metallic NW-catalyst seed 212. The secondary arms and subordinate arms of higher order of lower order may be provided by the method for fabricating the signal-amplification device 101 for SERS that includes growing an arm of higher order than the order of the main arm 140-1 at a site of a metallic NW-catalyst seed 212 to produce a MNSANW structure 140 with higher order arms than the main arm 140-1. Secondary arms and subordinate arms of higher order may be produced by a CVD process. Silane, $SiH_4$, is decomposed in a CVD chamber in which the combination of the NSA substrate 110, the plurality 120 of main arms and the plurality of metallic NW-catalyst seeds disposed on the surfaces of the main arms is placed. The cross-section through the metallic NW-catalyst seed 212 of the cross-sectional elevation view 200C is shown at the location of the trace of plane 2C-2C indicated in FIG. 2B. The metallic NW-catalyst seed 212 has a shape of an approximately spherical cap with height 290. The CVD of silane gives rise to the deposition of mobile silicon atoms on the surfaces of the plurality 120 of MNSANW structures, for example, MNSANW structures 130, 140 and 150. As shown in FIG. 2C, according to one model for the growth of nanowires, during CVD from silane, the silane preferentially decomposes at the metallic nanoparticles that serve as metallic NW-catalyst seeds, of which metallic NW-catalyst seed 212 is an example, rather than the regions free of metallic NW-catalyst seeds. The silicon atoms then diffuse through or around the metallic NW-catalyst seed, for example, metallic NW-catalyst seed 212, and precipitate on the main arm 140-1 to grow the secondary arm 140-2. Alternatively, according to another model for the growth of nanowires, which may be more appropriate to growth in a process employing molecular beam epitaxy (MBE), mobile silicon adatoms may be deposited on the surface 210 of the main arm 140-1 of MNSANW structure 140. These mobile silicon adatoms may then migrate to the base of the metallic NW-catalyst seed 212 and give rise to the growth of a secondary arm, for example, the secondary arm 140-2, on the surface of the main arm 140-1. The morphology of the secondary arm 140-2 grown on the main arm 140-1 is next described.

Figure 2D:
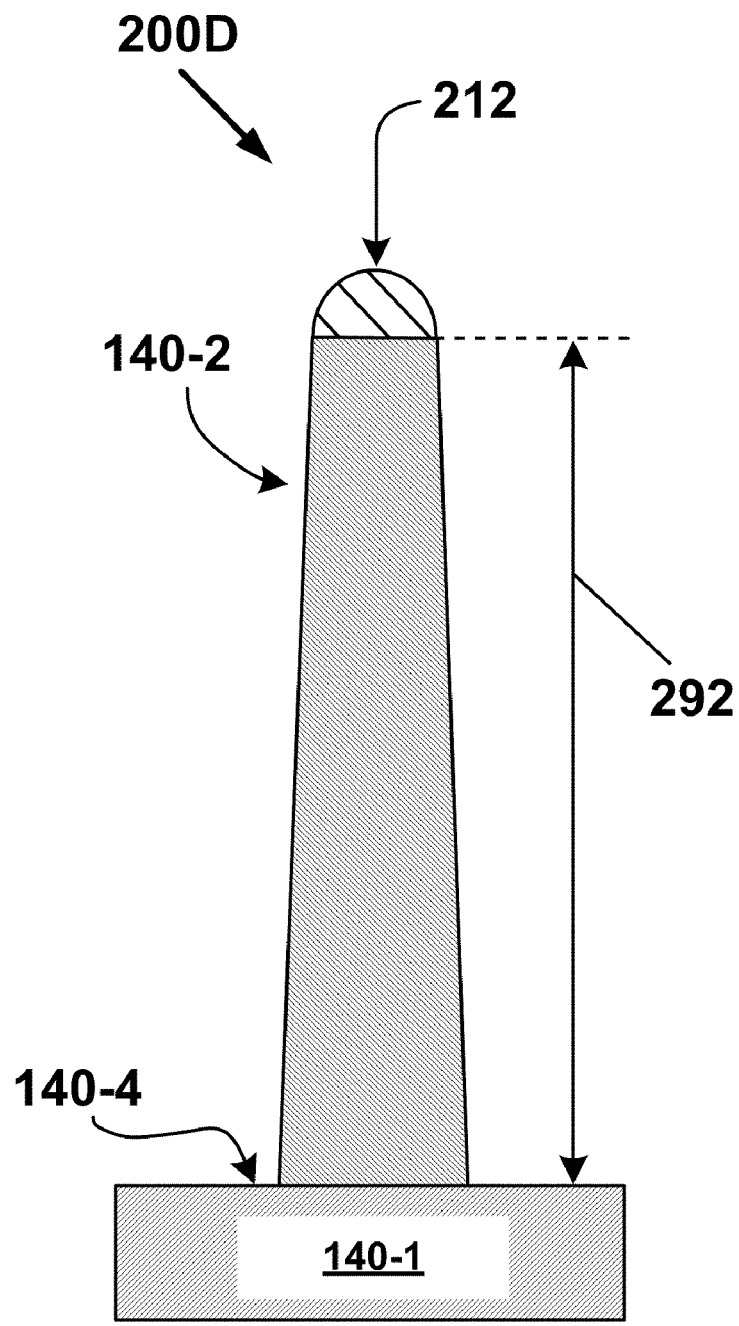
FIG. 2D is a cross-sectional elevation view of an arm of higher order than the order of the main arm at the site of the metallic NW-catalyst seed of FIGS. 2B and 2C illustrating the morphology of the arm of higher order after fabrication to produce a MNSANW structure with higher order arms than the main arm, in an embodiment of the present invention.

With reference now to FIG. 2D, in accordance with embodiments of the present invention, a cross-sectional elevation view 200D of an arm of higher order, for example, secondary arm 140-2, than the order of the main arm, for example, main arm 140-1, at a site of the metallic NW-catalyst seed, for example, metallic NW-catalyst seed 212, of FIGS. 2B and 2C is shown. FIG. 2D shows the morphology of the arm of higher order, for example, secondary arm 140-2, after fabrication to produce a MNSANW structure 140 with higher order arms than the main arm, for example, main arm 140-1. An example of the morphology of an arm of higher order than an order of the main arm 140-1 is that of a silicon nanowire. As shown in FIG. 2D, the secondary arm 140-2 includes a silicon nanowire of height 292. Thus, the plurality 142 of secondary arms, of which secondary arm 140-2 is an example, may be grown on the surface 140-4 of the main arm 140-1 of the MNSANW structure 140. The morphology of the plurality 142 of secondary arms grown on the main arm 140 is next described.

Figure 2E:
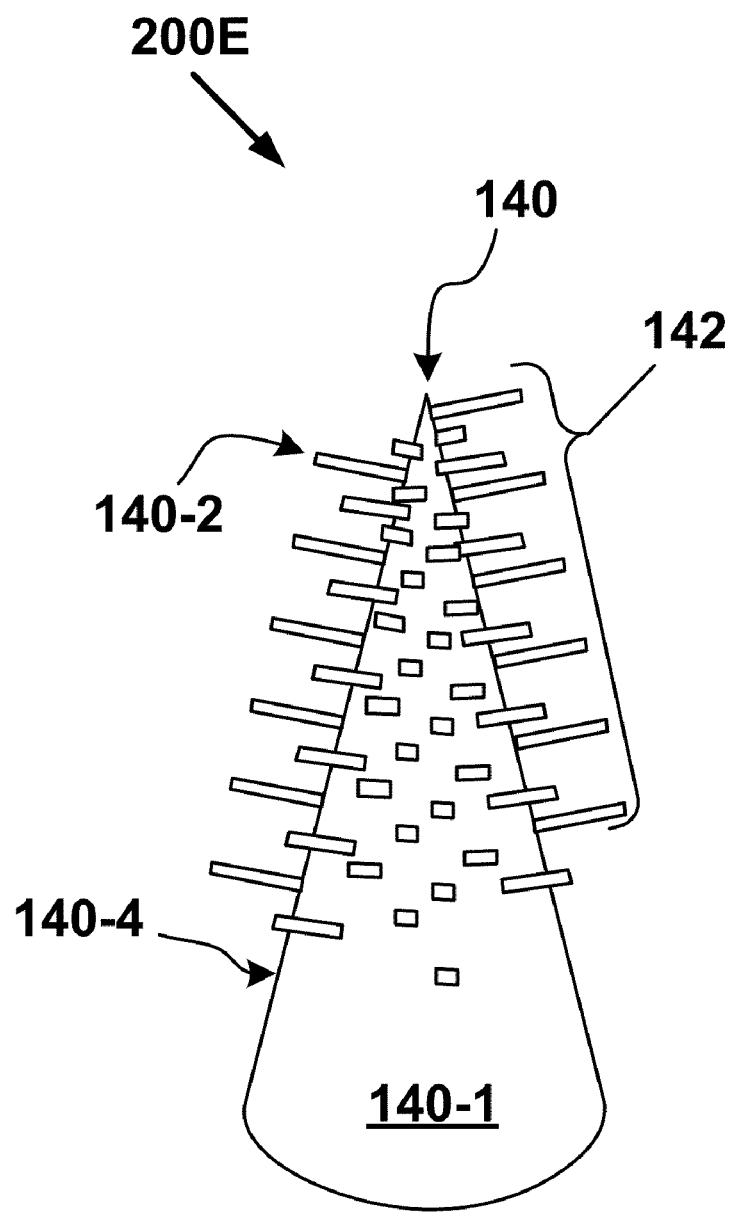
FIG. 2E is a perspective view of a plurality of arms of secondary order of the MNSANW structure of the signal-amplification device of FIGS. 1A and 1B illustrating the surface morphology of the MNSANW structure with the plurality of arms of at least secondary order disposed on the main arm, in an embodiment of the present invention.

With reference now to FIG. 2E, in accordance with embodiments of the present invention, a perspective view 200E of the plurality 142 of arms of secondary order of the MNSANW structure 140 of the signal-amplification device 101 of FIGS. 1A and 1B is shown. FIG. 2E shows the surface morphology of the MNSANW structure 140 with the plurality 142 of secondary arms, of which secondary arm 140-2 is an example, disposed on the main arm 140-1. The plurality 142 of secondary arms may be provided by the method for fabricating the signal-amplification device 101 for SERS that includes growing a secondary arm, for example, secondary arm 140-2, at a site of a metallic NW-catalyst seed on the main arm to produce a MNSANW structure 140 with secondary arms disposed on the main arm, for example, main arm 140-1. The plurality 142 of secondary arms may be produced by a CVD process. Silane, $SiH_4$, is decomposed in a CVD chamber in which the combination of the NSA substrate 110, the plurality 120 of main arms and the plurality of metallic NW-catalyst seeds disposed on the surfaces of the main arms is placed. As shown in FIGS. 2E and 2C, the plurality 142 of secondary arms, of which secondary arm 140-2 is an example, extend from the surface 210 (see FIG. 2C) of the main arm 140-1 of the MNSANW structure 140 in a direction that is determined primarily by the crystallographic orientation of the main arm 140-1. Although the plurality 142 of secondary arms is shown in FIG. 2E as being disposed normal to the surface 210 of the main arm 140-1, this is by way of example and not limitation thereto, as nanowires grow normal to the surface of a substrate under certain circumstances. In general, the orientation of a nanowire growing on the surface of the substrate depends upon the orientation of the substrate upon which the nanowire is grown. For example, nanowires often grow in <111> directions so that nanowires will grow at whatever angles the <111> directions may have within the substrate. For example, in the case of a silicon (001) substrate, silicon nanowires typically grow at approximately 55 degrees from the normal to the surface of the silicon (001) substrate. On the other hand in the case of a silicon (111) substrate, nanowires typically grow normal to the surface of the silicon (111) substrate. Moreover, although the plurality 142 of secondary arms is shown in FIG. 2E as being disposed on a single main arm, this is by way of example and not limitation thereto, as a plurality of secondary arms may be disposed on the entire surface 140-4 of the MNSANW structure 140, as well as the surfaces of the plurality 120 of MNSANW structures, which includes the surfaces of the plurality of main arms of the plurality 120 of MNSANW structures. Thus, in one embodiment of the present invention, the surface area of the MNSANW structure is increased by the additional surface area of the plurality 142 of secondary arms. In another embodiment of the present invention, the increased surface area of MNSANW structure 140 may provide a substrate for the further deposition of metallic SERS-active nanoparticles, similar to the metallic SERS-active nanoparticles shown in FIG. 2B. Thus, the method for fabricating the signal-amplification device 101 may include growing additional arms of higher order than the order of the main arm, for example, tertiary arms, at a site of a metallic NW-catalyst seed to produce a MNSANW structure with arms of higher order than the order of the main arm, as is next described.

Figure 2F:
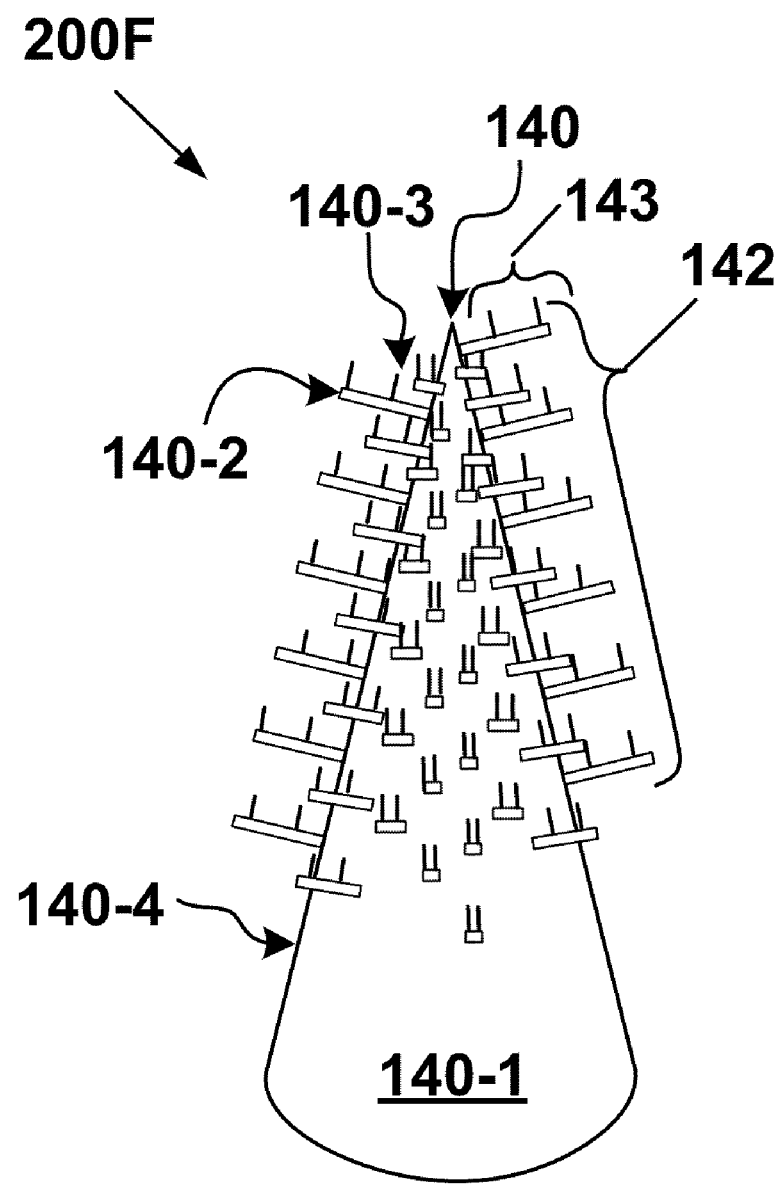
FIG. 2F is a perspective view of a plurality of subordinate arms of the MNSANW structure of the signal-amplification device of FIGS. 1A and 1B illustrating the surface morphology of the MNSANW structure with the plurality of subordinate arms disposed on an arm of lower order than an order of the subordinate arm, in an embodiment of the present invention.

With reference now to FIG. 2F, in accordance with embodiments of the present invention, a perspective view 200F of the plurality 143 of subordinate arms, of which tertiary arm 140-3 is an example, of the MNSANW structure 140 of the signal-amplification device 101 of FIGS. 1A and 1B is shown. FIG. 2F shows the surface morphology of the MNSANW structure 140 with the plurality 143 of subordinate arms. For example, the subordinate arm, for example, tertiary arm 140-3, may be disposed on an arm of lower order than an order of the subordinate arm, for example, secondary arm 140-2. The subordinate arms of higher order disposed on arms of lower order may be provided by the method for fabricating the signal-amplification device 101 that further includes: producing a plurality of metallic NW-catalyst seeds disposed on surfaces of MNSANW structures of the plurality of MNSANW structures; and, repeating growing an arm of higher order than the order of the main arm, in this case tertiary arm 140-3, at a site of a metallic NW-catalyst seed to produce a MNSANW structure with higher order arms than the main arm. In similar fashion to the production of secondary arms, the tertiary arms may be produced by a CVD process. Silane, $SiH_4$, is decomposed in a CVD chamber in which the combination of the NSA substrate 110, the plurality 120 of main arms, the plurality 142 of secondary arms and the plurality of metallic NW-catalyst seeds disposed on the surface 140-4 of the MNSANW structure 140 is placed. Thus, the MNSANW structure 140 includes both the main arm and the plurality 142 of secondary arms for the growth of the plurality 143 of tertiary arms disposed on a secondary arm of the plurality 142 of secondary arms. Although the plurality 143 of tertiary arms is shown in FIG. 2F as being disposed on a single secondary arm, this is by way of example and not limitation thereto, as a plurality of tertiary arms may be disposed on the entire surface 140-4 of the MNSANW structure 140, as well as the surfaces of the plurality 120 of MNSANW structures, which includes the surfaces of the plurality of main arms and the surfaces of the pluralities of secondary arms of the plurality 120 of MNSANW structures.

With further reference to FIG. 2F, in accordance with embodiments of the present invention, similar to FIG. 2E, the plurality 142 of secondary arms, of which secondary arm 140-2 is an example, extends from the surface 210 of the main arm 140-1 of the MNSANW structure 140 in a direction that is determined primarily by the crystallographic orientation of the main arm 140-1. In addition, the plurality 143 of tertiary arms, of which tertiary arm 140-3 is an example, extends from the surface of a lower order arm in a direction that is determined primarily by the crystallographic orientation of the lower order arm of the MNSANW structure 140, for example, the secondary arm 140-2. Thus, the surface area of the MNSANW structure is increased by the additional surface area of the plurality 143 of tertiary arms, as well as the plurality 142 of secondary arms. In one embodiment of the present invention, the arms may have different radii, which may serve to increase the Raman signal intensity. In another embodiment of the present invention, the increased surface area of MNSANW structure 140 may provide a substrate for the further deposition of metallic SERS-active nanoparticles, similar to the metallic SERS-active nanoparticles shown in FIG. 2B. The subordinate arms of higher order on arms of lower order may be provided by the method for fabricating the signal-amplification device 101 that, by way of example without limitation thereto, further includes: repeating producing a plurality of metallic NW-catalyst seeds disposed on surfaces of MNSANW structures of the plurality of MNSANW structures; and, repeating growing an arm of higher order, in this case a quaternary arm (not shown), than the order of the main arm at a site of a metallic NW-catalyst seed to produce a MNSANW structure with higher order arms than the main arm. In similar fashion to the production of tertiary arms, the quaternary arms may be produced by a CVD process. Silane, $SiH_4$, is decomposed in a CVD chamber in which the combination of the NSA substrate 110, the plurality 120 of main arms, the plurality 142 of secondary arms, the plurality 143 of tertiary arms and the plurality of metallic NW-catalyst seeds disposed on the surface 140-4 of the MNSANW structure 140 is placed. Thus, the MNSANW structure 140 includes the main arm, the plurality 142 of secondary arms and the plurality 143 of tertiary arms for the growth of a plurality of quaternary arms disposed on a tertiary arm and arms of lower order than tertiary. A plurality of quaternary arms may be disposed on the entire surface 140-4 of the MNSANW structure 140, as well as the surfaces of the plurality 120 of MNSANW structures, which includes the surfaces of the plurality of main arms, the pluralities of secondary arms and pluralities of tertiary arms of the plurality 120 of MNSANW structures. In accordance with embodiments of the present invention, producing a plurality of metallic NW-catalyst seeds disposed on surfaces of MNSANW structures of the plurality 120 of MNSANW structures, and growing an arm of higher order than the order of the main arm at a site of a metallic NW-catalyst seed to produce a MNSANW structure with higher order arms than the main arm may be repeated at least one time, or more than one time, to produce a plurality of subordinate arms on a MNSANW structure, for example, MNSANW structure 140. However, such repetitions are limited by the space remaining between arms of all orders of the plurality 120 of MNSANW structures, as is next described.

Figure 2G:
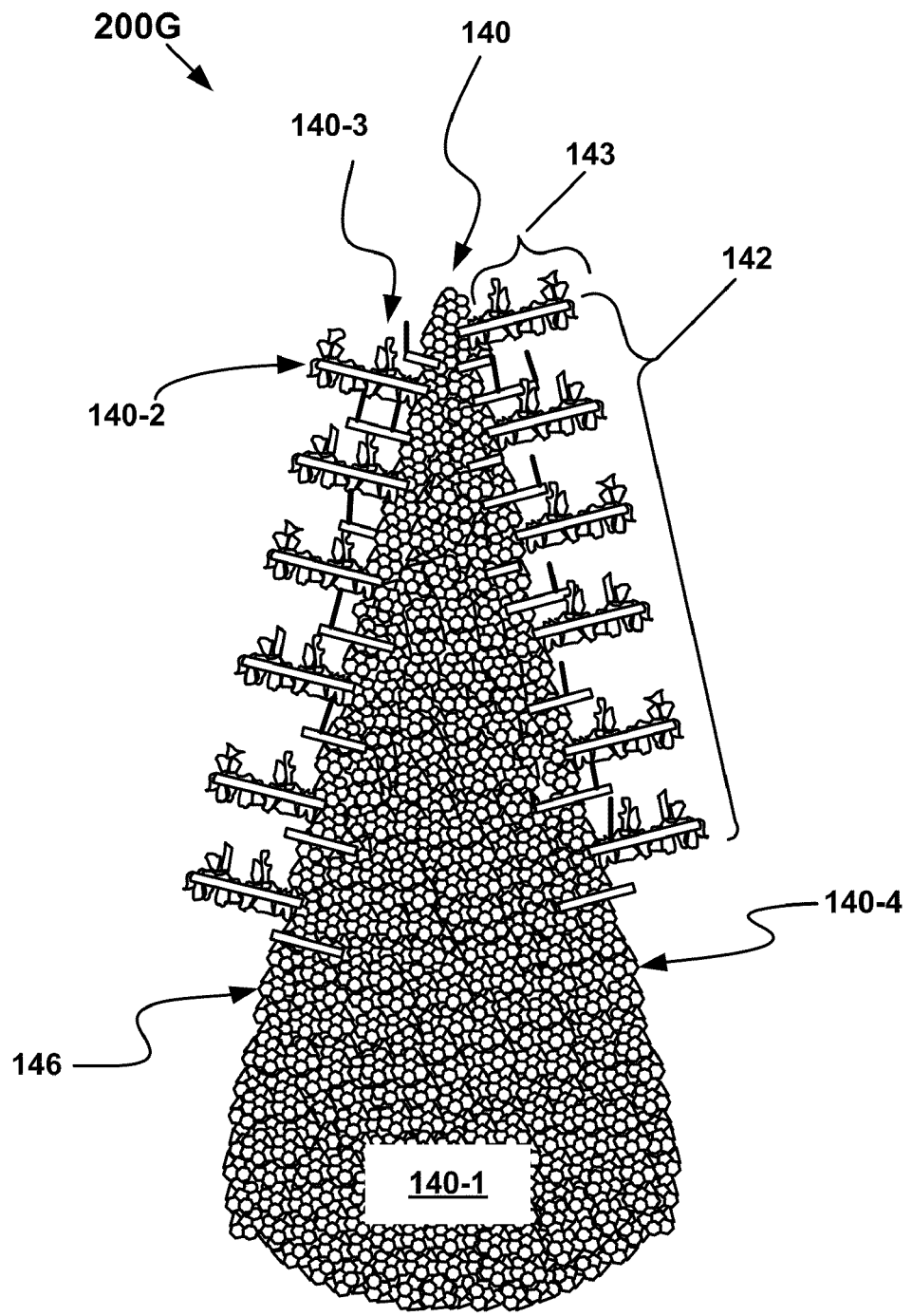
FIG. 2G is a perspective view of the main arm of the MNSANW structure of the signal-amplification device of FIGS. 1A and 1B illustrating the surface morphology of the MNSANW structure after depositing the plurality of metallic SERS-active nanoparticles on the surface of the MNSANW structure, in one embodiment of the present invention, and in another embodiment of the present invention, annealing the plurality of metallic SERS-active nanoparticles to agglomerate the metallic SERS-active nanoparticles and to coarsen a size of a metallic SERS-active nanoparticle of the plurality of metallic SERS-active nanoparticles.

With further reference to FIGS. 2E and 2F, in accordance with embodiments of the present invention, the morphology of the MNSANW structure 140 may be described as self-similar, because arms of higher order are arranged on arms of lower order. For example, the plurality 120 of main arms is disposed on the NSA substrate 110. Similarly, the plurality 142 of secondary arms is disposed on the surface 210 of the main arm 140, which arrangement also applies to pluralities of secondary arms disposed on the surfaces of other main arms, for example, main arms 130-1 and 150-1. Similarly, the plurality 143 of tertiary arms is disposed on the surface of a secondary arm, which arrangement also applies to pluralities of tertiary arms disposed on the surfaces of other secondary arms. However, the shapes of secondary and higher order arms than secondary arms may be different than the shape of the main arm 140-1. The direction that secondary and higher order arms will take will be controlled by the crystallographic orientation of a nanowire on the arm of lower order, upon which the nanowire, for example, secondary and higher order arms, are grown. Thus, the direction at which secondary and higher order arms grow relative to the surface of an underlying arm of lower order, upon which a secondary or higher order arm may grow, may be different for arms of different order depending on directions corresponding to the nanowire growth direction, for example, the [111] growth directions discussed above. Consequently, the arrangement of the arms is not necessarily normal to the surface of lower order arms as shown in FIGS. 2E-2G, which is consequently by way of example and not limitation thereto. Therefore, the morphology of the MNSANW structure 140, as well as other MNSANW structures, for example, MNSANW structures 130 and 150, is similar to that of a fractal structure. However, the MNSANW structures are not truly fractal, because the MNSANW structures are not self-similar on all spatial scales; in particular, the number of spatial scales is limited to the number of tiers, which is defined by the number of orders of arms, which may be practically about three. Classical surfaces are two-dimensional; and therefore, classical surfaces have a dimension of two. On the other hand, volumes are three-dimensional; and therefore, volumes have a dimension of three. However, fractal structures are characterized by fractal dimensions which are intermediate between such integral values. Thus, the surface of the signal-amplification device 101 for SERS is characterized by a surface area that may have a fractal dimension greater than two. Moreover, the surface of the signal-amplification device 101 for SERS is also characterized by a surface area that may have a fractal dimension less than three. However, it may be seen that in proximity to the location of the bases of the plurality of main arms, for example, main arms 130-1, 140-1 and 150-1, disposed on the NSA substrate 110, there is limited space to accommodate the growth of arms of higher order. Therefore, unlimited successive repetitions of the growth of subordinate arms might possibly result in a space filling structure, so that there would be no surface area to accommodate the deposition of pluralities of metallic SERS-active nanoparticles that serve to enhance a Raman spectrum of a molecule disposed in proximity to a metallic SERS-active nanoparticle, which is next described.

With reference now to FIG. 2G, in accordance with embodiments of the present invention, a perspective view 200G of the main arm 140-1 of a MNSANW structure 140 of the signal-amplification device 101 of FIGS. 1A and 1B is shown. FIG. 2G shows the surface morphology of the MNSANW structure 140 after depositing a plurality of metallic SERS-active nanoparticles on a surface 140-4 of the MNSANW structure 140, in one embodiment of the present invention, and in another embodiment of the present invention, annealing the plurality of metallic SERS-active nanoparticles to agglomerate the metallic SERS-active nanoparticles and to coarsen a size of a metallic SERS-active nanoparticle of the plurality of metallic SERS-active nanoparticles. In another embodiment of the present invention, an annealing may be used to agglomerate the metallic NW-catalyst seeds and to coarsen a size of the metallic NW-catalyst seeds. The annealing applied to the metallic NW-catalyst seeds may be the same as that applied to the plurality of metallic SERS-active nanoparticles, particularly if the composition of the metallic NW-catalyst seeds is the same as the composition of the metallic SERS-active nanoparticles. However, if the composition of the metallic NW-catalyst seeds differs from that of the metallic SERS-active nanoparticles, the annealing conditions for the metallic NW-catalyst seeds may differ from the annealing conditions for the metallic SERS-active nanoparticles. Annealing to agglomerate the metallic SERS-active nanoparticles is mainly applicable to a thin, physically deposited metal layer. Annealing may also improve contact to an underlying lower-order arm. The plurality of metallic SERS-active nanoparticles, of which metallic SERS-active nanoparticle 146 is an example, disposed on a surface of the MNSANW structure, for example, surface 140-4 of MNSANW structure 140, may be provided by the method for fabricating the signal-amplification device 101 that further includes: depositing a plurality of metallic SERS-active nanoparticles on a surface of the MNSANW structure; and, annealing the plurality of metallic SERS-active nanoparticles to agglomerate the metallic SERS-active nanoparticles on the surface of the MNSANW structure and to coarsen a size of a metallic SERS-active nanoparticle of the plurality of metallic SERS-active nanoparticles. In another embodiment of the present invention, the method for fabricating the signal-amplification device 101 may further include: annealing the metallic NW-catalyst seeds to agglomerate the metallic NW-catalyst seeds on the surface of the MNSANW structure and to coarsen a size of a metallic NW-catalyst seeds. The plurality of metallic SERS-active nanoparticles may be deposited on the surface of the MNSANW structure by a variety of techniques, by way of example without limitation thereto: CVD, as previously discussed in the description of the production of metallic NW-catalyst seeds disposed on surfaces of main arms; PVD, by sputtering; PVD by evaporation, for example, electron beam (e-beam) evaporation; and, electrochemical deposition, for example, electroplating. However, in employing these various deposition techniques, the amount of material deposited is controlled to avoid the coalescence of the deposited material into a continuous film. Annealing may be employed in conjunction with deposition, or alternatively after deposition has been completed, to cause the metallic SERS-active nanoparticles to agglomerate on the surface of the MNSANW structure, for example, surface 140-4 of MNSANW structure 140. In another embodiment of the present invention, annealing may also be employed to cause the metallic NW-catalyst seeds to agglomerate on the surface 140-4 of the MNSANW structure 140 and to coarsen a size of a metallic NW-catalyst seeds. The temperature and time of the annealing is controlled to avoid the formation of excessively large particles. Rather, a process similar to Ostwald ripening may be employed to consume the smallest of the metallic SERS-active nanoparticles giving a surface morphology of the distribution of the metallic SERS-active nanoparticles on the surface of the MNSANW structure, for example, surface 140-4 of MNSANW structure 140, that provides an approximately uniform dispersion of metallic SERS-active nanoparticles having a size larger than the smallest metallic SERS-active nanoparticles of an initial deposit. Therefore, as shown in FIG. 2G, the entire surface 140-4 of the MNSANW structure 140, including the surface 210 of the main arm and the surfaces of the subordinate arms, may be covered with a dispersion of metallic SERS-active nanoparticles. In one embodiment of the present invention, a metallic SERS-active nanoparticle, for example, metallic SERS-active nanoparticle 146, of the plurality of metallic SERS-active nanoparticles may be composed of a noble metal constituent. In another embodiment of the present invention, a metallic SERS-active nanoparticle, for example, metallic SERS-active nanoparticle 146, of the plurality of metallic SERS-active nanoparticles may be composed of a constituent selected from the group of constituents consisting of copper, silver, gold, aluminum, tungsten, palladium, platinum and mercury.

Figure 3:
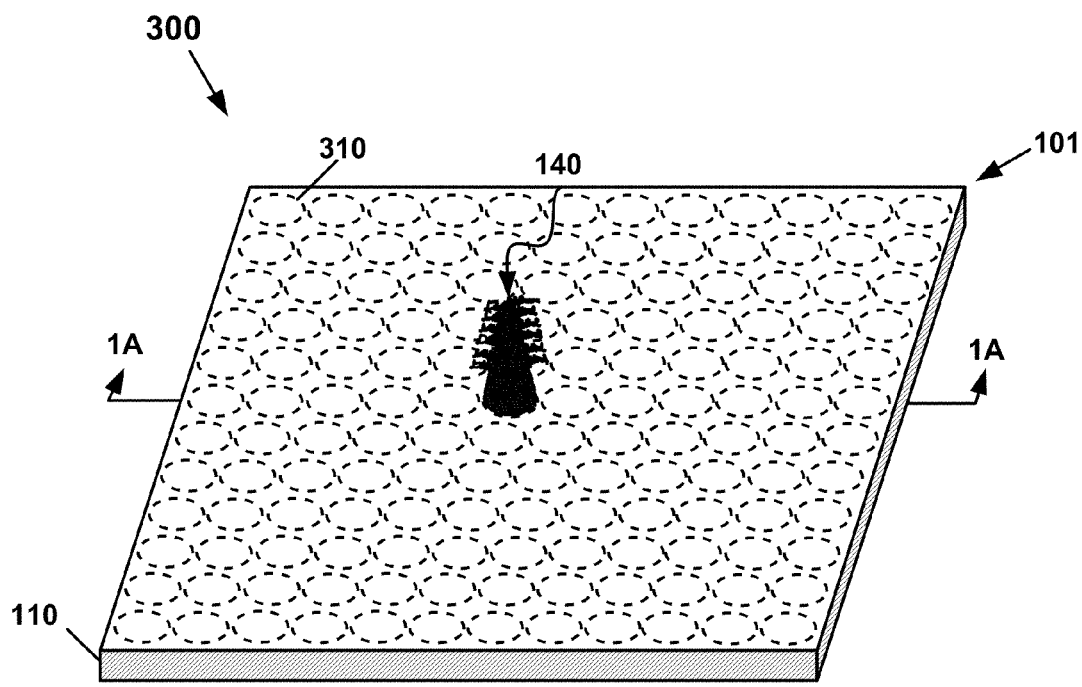
FIG. 3 is a perspective view of the MNSANW structure of the signal-amplification device of FIGS. 1A and 1B illustrating the configuration of MNSANW structures on the NSA substrate and the location of a cross-section shown in FIGS. 1A and 1B of the signal-amplification device, in an embodiment of the present invention.

With further reference to FIGS. 1A and 1B and with reference now to FIG. 3, in accordance with embodiments of the present invention, a perspective view 300 of MNSANW structure 140 of the signal-amplification device 101 of FIGS. 1A and 1B is shown. FIG. 3 shows the configuration of MNSANW structures on the NSA substrate 110, of which MNSANW structure 140 is an example. FIG. 3 also shows the location of the cross-section for the cross-sectional elevation views 100A and 100B shown respectively in FIGS. 1A and 1B of the signal-amplification device 101. The MNSANW structure 140 is shown in detail in FIG. 3; but, so as not to obscure FIG. 3 with excessive details, only the silhouettes of the bases (shown as dashed circles) of other MNSANW structures are shown. The trace of a plane 1A-1A that indicates the location of a cross-section through a row of MNSANW structures is also shown in FIG. 3; the location of the cross-section, which is given by the trace of the plane 1A-1A, passes through the MNSANW structures 130, 140 and 150 of the cross-sectional elevation views 100A and 100B of FIGS. 1A and 1B, respectively. Although the arrangement of the plurality 120 of MNSANW structures, for example, MNSANW structures 130, 140 and 150, on the NSA substrate 110 is shown as a regularly repeating two-dimensional array over the surface of the NSA substrate 110, this is by way of example and not limitation, as other arrangements of the plurality 120 of MNSANW structures are within the spirit and scope of embodiments of the present invention. For example, the arrangement of the plurality 120 of MNSANW structures on black silicon is likely random. Moreover, although the heights of the plurality 120 of MNSANW structures shown in FIGS. 1A and 1B is shown as being constant, this is also by way of example and not limitation, as the heights of individual MNSANW structures within the plurality 120 of MNSANW structures may vary from MNSANW structure to MNSANW structure across the surface of the NSA substrate 110. Thus, the variation of the heights of individual MNSANW structures within the plurality of MNSANW structures and the variation in the arrangement of individual MNSANW structures across the surface of the NSA substrate 110 are similarly within the spirit and scope of embodiments of the present invention, as might be expected if black silicon is utilized to provide the plurality of main arms of the plurality 120 of MNSANW structures on the NSA substrate 110. Also, the aspect ratio of the base to the height of the MNSANW structure 140 as shown in FIG. 3 has been altered from the aspect ratio of a main arm that is expected for an asperity of black silicon in order to highlight the morphology and surface structure of the MNSANW structure 140. Thus, in an embodiment of the present invention, the signal-amplification device 101 for SERS includes the NSA substrate 110, the plurality 120 of MNSANW structures, as described in the discussion of FIGS. 1A-2G, and the plurality of metallic SERS-active nanoparticles, as described in the discussions of FIGS. 1B and 2G. The arrangement of the plurality 120 of MNSANW structures including metallic SERS-active nanoparticles of the signal-amplification device 101 for use in a spectroscopic analysis device to enhance a Raman spectrum of a molecule disposed in proximity to a metallic SERS-active nanoparticle is next described.

Figure 4A:
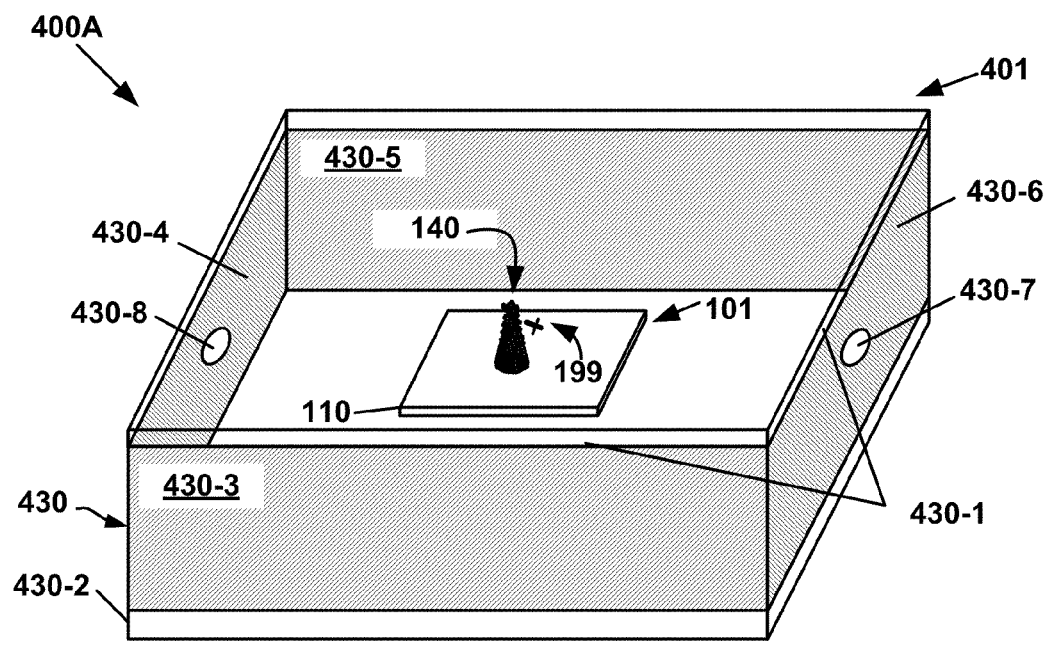
FIG. 4A is a perspective view of a spectroscopic analysis cell including the signal-amplification device of FIGS. 1A, 1B and 3, and an enclosure encapsulating the signal-amplification device illustrating the configuration of the enclosure for confining the molecule of the molecular constituent for SERS within the enclosure, in an embodiment of the present invention.

With reference now to FIG. 4A, in accordance with embodiments of the present invention, a perspective view 400A of a spectroscopic analysis cell 401 of a spectroscopic analysis device 402 (shown in FIG. 4B) that includes the signal-amplification device 101 of FIGS. 1A, 1B and 3, and may also include an enclosure 430 encapsulating the signal-amplification device 101 is shown. FIG. 4A shows the configuration of the enclosure 430 for confining the molecule 199 of a molecular constituent for SERS within the enclosure 430. The spectroscopic analysis cell 401 includes the signal-amplification device 101 for SERS. In another embodiment of the present invention, the spectroscopic analysis cell 401 may also include the enclosure 430 encapsulating the signal-amplification device 101; the enclosure 430 is also configured to confine a molecule of a molecular constituent for SERS within the enclosure 430. As previously described in the above discussion of FIGS. 1A-3, the signal-amplification device 101 includes a NSA substrate 110, the plurality 120 of MNSANW structures, and a plurality of metallic SERS-active nanoparticles. The enclosure 430 includes a window 430-1, a platform 430-2, sidewalls 430-3, 430-4, 430-5 and 430-6 and an inlet 430-7. The window 430-1 is transparent, as indicated by the shading lines, to both exciting electromagnetic radiation that may be used to excite the molecule and emitted electromagnetic radiation that may be emitted from the molecule in response to the exciting electromagnetic radiation. The platform 430-2 is attached to the signal-amplification device 101. The sidewalls 430-3, 430-4, 430-5 and 430-6 are attached to the window 430-1 and attached to the platform 430-2. The sidewalls 430-3, 430-4, 430-5 and 430-6, as well as the window 430-1 and platform 430-2, are configured to confine the molecule within the enclosure 430. The inlet 430-7 is configured to admit a fluid (not shown) into the enclosure 430. The fluid may include a carrier fluid and a molecular constituent, a molecule 199 of which may be subjected to Raman spectroscopic analysis. The enclosure 430 may further include an outlet 430-8. The outlet 430-8 is configured to remove the carrier fluid from the enclosure 430. The fluid may be a fluidic species selected from the group of fluidic species consisting of a liquid, a gas and a mixture of a liquid and a gas.

Figure 4B:
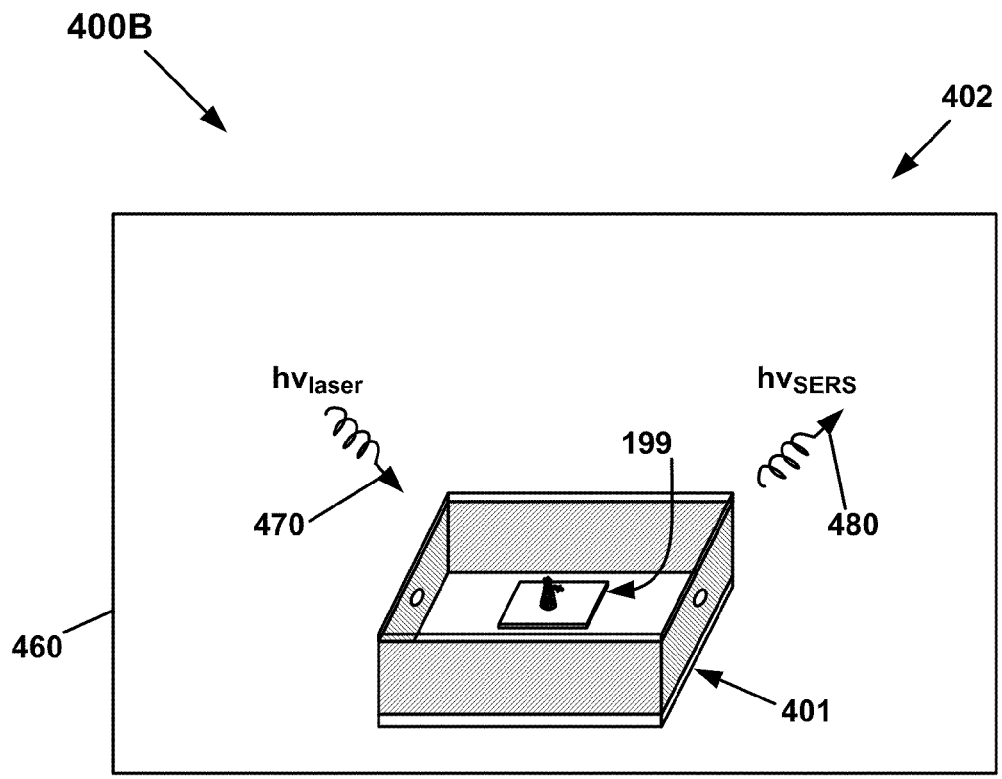
FIG. 4B is a block diagram of the spectroscopic analysis device for SERS including the spectroscopic analysis cell of FIG. 4A and a Raman spectrometer illustrating the configuration of the Raman spectrometer for accepting the spectroscopic analysis cell for SERS of the molecule confined within the spectroscopic analysis cell, in an embodiment of the present invention.

With reference now to FIG. 4B, in accordance with embodiments of the present invention, a block diagram 400B of the spectroscopic analysis device 402 for SERS including the spectroscopic analysis cell 401 of FIG. 4A and a Raman spectrometer 460 is shown. FIG. 4B shows the configuration of the Raman spectrometer 460 for accepting the spectroscopic analysis cell 401 for SERS of molecule 199 confined within the spectroscopic analysis cell 401. The spectroscopic analysis device 402 for SERS includes the spectroscopic analysis cell 401 and the Raman spectrometer 460. The Raman spectrometer 460 is configured to accept the spectroscopic analysis cell 401. The Raman spectrometer 460 includes a source of exciting electromagnetic radiation 470 that is used to excite the molecule 199. The source of exciting electromagnetic radiation 470 may be a laser (not shown). The energy of a photon of the exciting electromagnetic radiation 470 is given by Planck's constant times the frequency of the laser source, given by: $h\nu_{laser}$. In addition, the Raman spectrometer 460 includes an analyzer (not shown) and a detector (not shown) that are used to analyze and detect emitted electromagnetic radiation 480. The Raman scattered electromagnetic radiation 480 emerges from the molecule 199 in response to the exciting laser source. The energy of a photon of the emitted electromagnetic radiation 480 from the molecule 199 is given by Planck's constant times the frequency of the molecular source, given by: $h\nu_{SERS}=h\nu_o \pm h\Delta$ where $\nu_o$ is the frequency of the incident laser field and $\Delta$ the Raman shift. Because of the interaction with surface plasmons excited in the plurality of metallic SERS-active nanoparticles, the magnitude of the local electric field $E_{molecule}$, at a molecule 199, is enhanced compared to the incident field $E_o$. Thus, the cross section of the SERS interaction, $\sigma_{SERS}$, scales as the fourth power of the electric field at the molecule 199, so that approximately: $\sigma_{SERS}=k\,E_{molecule}^4$, where k is a constant of proportionality.

With further reference to FIG. 4B, in accordance with embodiments of the present invention, to enhance the magnitude of the electric field vector at the molecule 199 the size of the metallic SERS-active nanoparticle is small to increase the surface curvature; and, the linear dimension of the metallic SERS-active nanoparticle is much less than the wavelength of the exciting electromagnetic radiation 470. Similarly, in accordance with an embodiment of the present invention, to enhance the magnitude of the electric field vector of the electromagnetic radiation emitted from the molecule 199, the size of the metallic SERS-active nanoparticle is less than the wavelength of the electromagnetic radiation emitted from the molecule 199. In accordance with an embodiment of the present invention, the composition of a metallic SERS-active nanoparticle is such that the surface plasmons excited in the metallic SERS-active nanoparticle are within the wavelength ranges of the exciting electromagnetic radiation 470 and the electromagnetic radiation emitted from the molecule 199; these wavelength ranges may extend from the near ultraviolet to the near infrared. Thus, in accordance with embodiments of the present invention, the plurality of metallic SERS-active nanoparticles may be composed of a noble metal constituent; or alternatively, the plurality of metallic SERS-active nanoparticles may be composed of a constituent selected from the group of constituents consisting of copper, silver, gold, aluminum, tungsten, palladium, platinum and mercury. In accordance with an embodiment of the present invention, the signal associated with the emitted electromagnetic radiation 480 is amplified by increasing the density of metallic SERS-active nanoparticles on the surface in proximity to which a molecule is disposed. Embodiments of the present invention increase the number of metallic SERS-active nanoparticles in proximity to a molecule disposed on the surface of the signal-amplification device 101 by employing MNSANW structures having a large surface area upon which the plurality of metallic SERS-active nanoparticles may be disposed. Correspondingly, in accordance with embodiments of the present invention, due to the increased number of metallic SERS-active nanoparticles, an increase in the excitation of surface plasmons in proximity to the molecule 199 is expected to amplify the signal from the molecule 199 in SERS beyond what is expected for a surface covered by a plurality of metallic SERS-active nanoparticles that are not disposed on MNSANW structures. Therefore, embodiments of the present invention provide a signal-amplification device for SERS.

With further reference to FIG. 4B, in accordance with embodiments of the present invention, the spectroscopic analysis cell 401 of the spectroscopic analysis device 402 may be configured as a cartridge that may be inserted into the Raman spectrometer 460. Moreover, the spectroscopic analysis cell 401 may further include a disposable cartridge to facilitate the analysis of molecule 199 of a molecular constituent. The disposition of the molecule 199 in proximity to a metallic SERS-active nanoparticle may be caused by the phenomenon of adsorption. Adsorption of a molecule on the surface of a metallic SERS-active nanoparticle or plurality of metallic SERS-active nanoparticles may occur by either the mechanism of chemisorption or physisorption. Thus, in accordance with embodiments of the present invention, a spectroscopic analysis cell 401 may be disposed as a witness device in a chemical environment for the collection of molecules by adsorption of a molecular constituent prior to insertion into the Raman spectrometer 460 for analysis, in which case the spectroscopic analysis cell 401 might not include the enclosure 430.

Figure 5:
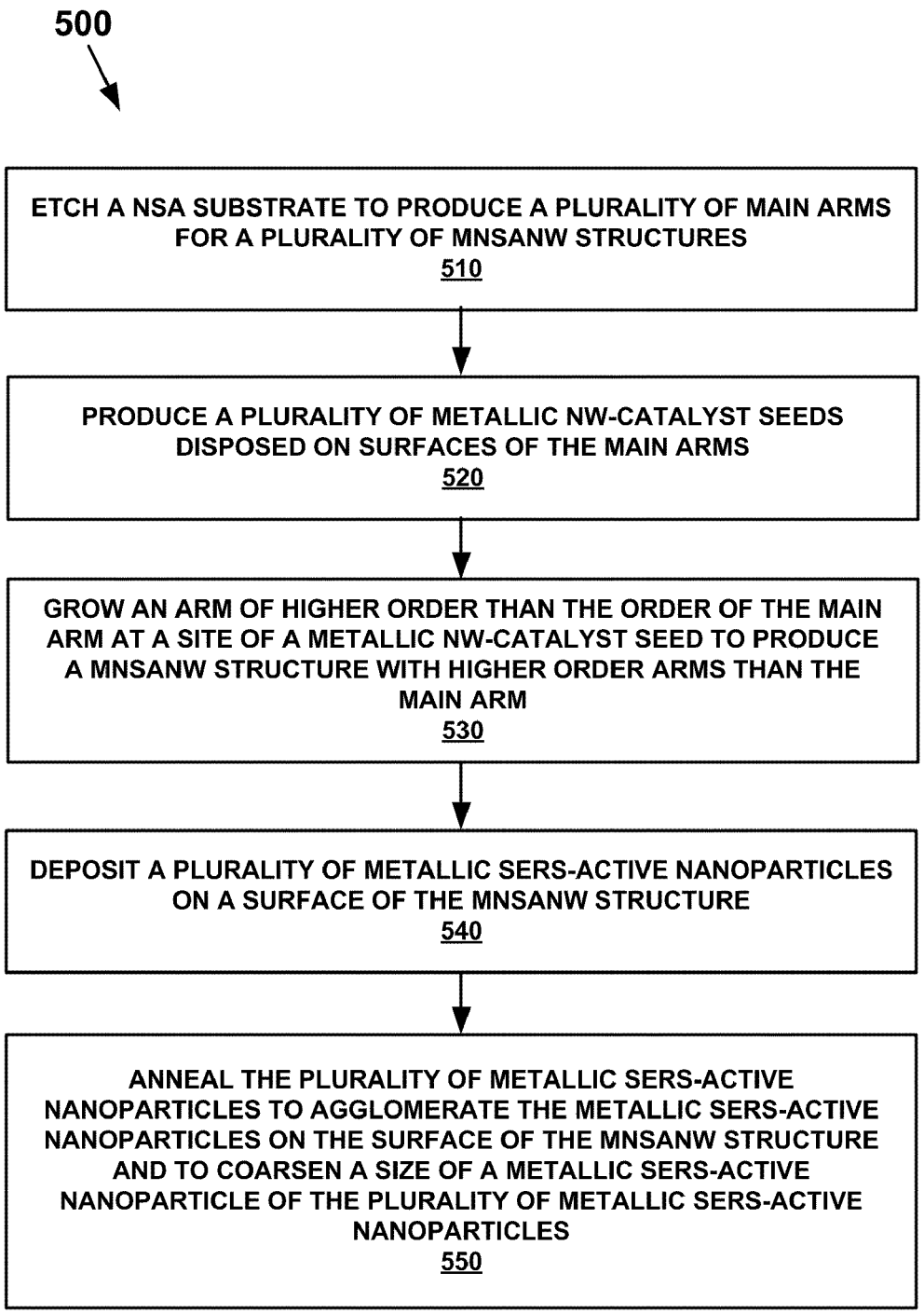
FIG. 5 is a flow chart for a method of fabricating the signal-amplification device of FIGS. 1A through 4B for SERS, in an embodiment of the present invention.

With reference now to FIG. 5, in accordance with embodiments of the present invention, a flow chart for a method of fabricating the signal-amplification device of FIGS. 1A through 4B for SERS is shown. The method for fabricating a signal-amplification device for SERS includes the following. At 510, a NSA substrate is etched to produce a plurality of main arms for a plurality of MNSANW structures. At 520, a plurality of metallic NW-catalyst seeds is produced that is disposed on surfaces of the main arms. The metallic NW-catalyst seeds may be composed of a constituent selected from the group of constituents consisting of aluminum, silver, gold, platinum, palladium, titanium and nickel. At 530, an arm of higher order than the order of the main arm is grown at a site of a metallic NW-catalyst seed to produce a MNSANW structure with higher order arms than the main arm. At 540, a plurality of metallic SERS-active nanoparticles is disposed on a surface of the MNSANW structure. The surface of the signal-amplification device for SERS is characterized by a surface area that may have a fractal dimension greater than two, but less than three. Additionally, in another embodiment of the present invention, at 550, the plurality of metallic SERS-active nanoparticles may be annealed to agglomerate the metallic SERS-active nanoparticles on the surface of the MNSANW structure and to coarsen a size of a metallic SERS-active nanoparticle of the plurality of metallic SERS-active nanoparticles. Moreover, in another embodiment of the present invention, the method for fabricating the signal-amplification device 101 may further include: annealing the metallic NW-catalyst seeds to agglomerate the metallic NW-catalyst seeds on the surface of the MNSANW structure and to coarsen a size of a metallic NW-catalyst seeds.

Figure 6:
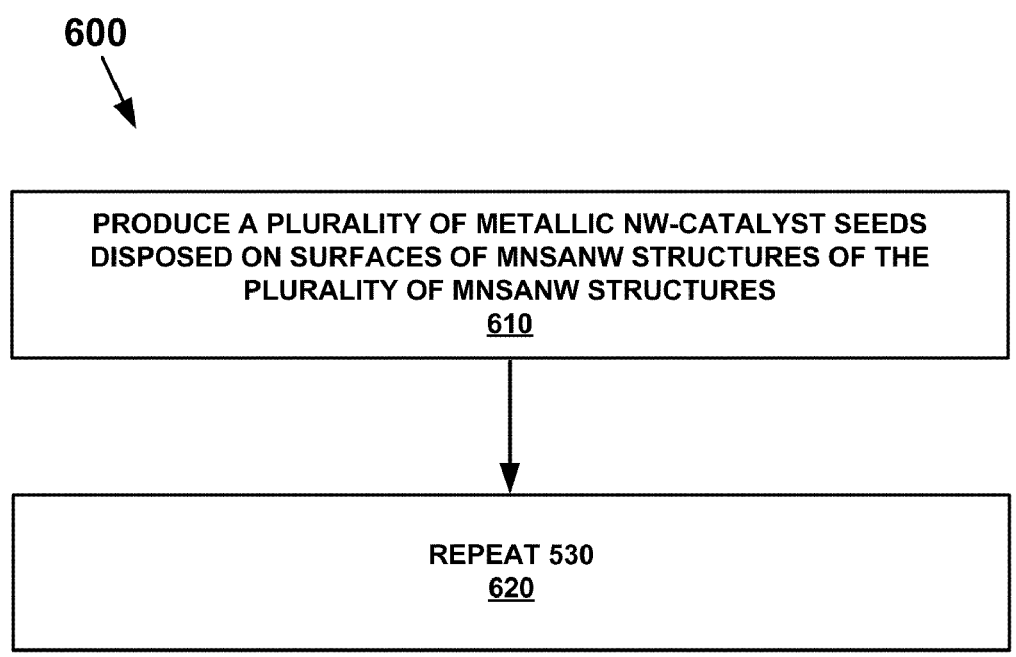
FIG. 6 is a flow chart of further embodiments of the method of FIG. 5 for fabricating the signal-amplification device for SERS, in an embodiment of the present invention.

With reference now to FIGS. 6 and 7, in accordance with embodiments of the present invention, flow charts of further embodiments of the method of FIGS. 5 and 6, respectively, for fabricating the signal-amplification device for SERS are shown. In one embodiment of the present invention, the method of fabricating the signal-amplification device may also include the following. At 610, a plurality of metallic NW-catalyst seeds is produced that is disposed on surfaces of MNSANW structures of the plurality of MNSANW structures. At 620, 530 is repeated so that: an arm of higher order than the order of the main arm is grown at a site of a metallic NW-catalyst seed to produce a MNSANW structure with higher order arms than the main arm. Alternatively, in another embodiment of the present invention, the method of fabricating the signal-amplification device may include the following. At 710, both 610 and 620 are repeated at least one time so that: a plurality of metallic NW-catalyst seeds is produced that is disposed on surfaces of MNSANW structures of the plurality of MNSANW structures; and, an arm of higher order than the order of the main arm is grown at a site of a metallic NW-catalyst seed to produce a MNSANW structure with higher order arms than the main arm. In accordance with embodiments of the present invention, both 610 and 620 may be repeated more than once, as previously described.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments described herein were chosen and described in order to best explain the principles of the invention and its practical application, to thereby enable others skilled in the art to best utilize the invention and various embodiments with various modifications as are suited to the particular use contemplated. It may be intended that the scope of the invention be defined by the claims appended hereto and their equivalents.

What is claimed is:

1. A signal-amplification device for surface enhanced Raman spectroscopy (SERS), said signal-amplification device comprising:
    a non-SERS-active substrate;
    a plurality of multi-tiered non-SERS-active nanowire structures, a multi-tiered non-SERS-active nanowire structure of said plurality of structures comprising:
        a main arm of a plurality of main arms, said plurality of main arms disposed on said non-SERS-active substrate; and
        a plurality of arms of at least secondary order, a secondary arm of said plurality of arms disposed on said main arm; and
    a plurality of metallic SERS-active nanoparticles, a metallic SERS-active nanoparticle of said plurality of metallic SERS-active nanoparticles disposed on a surface of said structure; and
    wherein said plurality of main arms disposed on said non-SERS-active substrate comprises black silicon.

2. The signal-amplification device of claim 1, wherein at least one main arm of said plurality of main arms has a substantially conical shape.

3. The signal-amplification device of claim 1, wherein at least one metallic SERS-active nanoparticle of said plurality of metallic SERS-active nanoparticles is configured to enhance a Raman spectrum of a molecule disposed in proximity to said metallic SERS-active nanoparticle.

4. The signal-amplification device of claim 1, wherein at least one metallic SERS-active nanoparticle of said plurality of metallic SERS-active nanoparticles is composed of a noble metal constituent.

5. The signal-amplification device of claim 1, wherein at least one metallic SERS-active nanoparticle of said plurality of metallic SERS-active nanoparticles is composed of a constituent selected from the group of constituents consisting of copper, silver, gold, aluminum, tungsten, palladium, platinum and mercury.

6. The signal-amplification device of claim 1, wherein said structure of said plurality of structures further comprises:
    a plurality of subordinate arms,
    wherein a subordinate arm of said plurality of subordinate arms is selected from the group consisting of tertiary arms, quaternary arms and arms of higher order than quaternary, and wherein a subordinate arm of said plurality of subordinate arms is disposed on an arm of lower order than an order of said subordinate arm.

7. The signal-amplification device of claim 1, wherein an arm of higher order than an order of said main arm further comprises a silicon nanowire.

8. A method for fabricating a signal-amplification device for SERS, said method comprising:
    a) etching a non-SERS-active substrate to produce a plurality of main arms for a plurality of structures;
    b) producing a plurality of metallic nanowire-catalyst seeds disposed on surfaces of said main arms;
    c) growing an arm of higher order than an order of said main arm at a site of a metallic nanowire-catalyst seed to produce a multi-tiered non-SERS-active nanowire structure with higher order arms than said main arm; and
    d) depositing a plurality of metallic SERS-active nanoparticles on a surface of said structure; and
    wherein said plurality of main arms disposed on said non-SERS-active substrate comprises black silicon.

9. The method of claim 8, further comprising:
    e) annealing said plurality of metallic SERS-active nanoparticles to agglomerate said metallic SERS-active nanoparticles on said surface of said structure and to coarsen a size of a metallic SERS-active nanoparticle of said plurality of metallic SERS-active nanoparticles.

10. The method of claim 8, further comprising:
    f) producing a plurality of metallic nanowire-catalyst seeds disposed on surfaces of structures of said plurality of structures; and
    g) repeating c).

11. The method of claim 10, further comprising repeating f) and g) at least one time to produce a plurality of subordinate arms on said structure.

12. The method of claim 8, wherein a surface of said signal-amplification device for SERS is characterized by a surface area that has a fractal dimension greater than two, but less than three.

13. The method of claim 8, wherein said metallic nanowire-catalyst seeds are composed of a constituent selected from the group of constituents consisting of aluminum, silver, gold, platinum, palladium, titanium and nickel.

14. A spectroscopic analysis device for SERS, said spectroscopic analysis device comprising:
    a spectroscopic analysis cell comprising:
        a signal-amplification device for SERS, said signal-amplification device comprising:
            a non-SERS-active substrate;
            a plurality of multi-tiered non-SERS-active nanowire structures, a multi-tiered non-SERS-active nanowire structure of said plurality of structures comprising:
                a main arm of a plurality of main arms, said plurality of main arms disposed on said non-SERS-active substrate; and
                at least a plurality of secondary arms, a secondary arm of said plurality of secondary arms disposed on said main arm; and
            a plurality of metallic SERS-active nanoparticles, a metallic SERS-active nanoparticle of said plurality of metallic SERS-active nanoparticles disposed on a surface of said structure; and wherein said plurality of main arms disposed on said non-SERS-active substrate comprises black silicon.

15. The spectroscopic analysis device of claim 14, wherein said spectroscopic analysis cell further comprises:

an enclosure encapsulating said signal-amplification device and configured to confine a molecule of a molecular constituent for SERS within said enclosure.

16. The spectroscopic analysis device of claim 15, wherein said enclosure further comprises:

a window that is transparent to both exciting electromagnetic radiation that may be used to excite said molecule and emitted electromagnetic radiation that may be emitted from said molecule in response to said exciting electromagnetic radiation;

a platform attached to said signal-amplification device;

sidewalls attached to said window and attached to said platform, said sidewalls configured to confine said molecule within said enclosure;

an inlet configured to admit a fluid into said enclosure, said fluid comprising a carrier fluid and said molecular constituent.

17. The spectroscopic analysis device of claim 16, wherein said enclosure further comprises:

an outlet configured to remove said carrier fluid from said enclosure.

18. The spectroscopic analysis device of claim 14, wherein said spectroscopic analysis cell is configured as a disposable cartridge that may be inserted into a Raman spectrometer.

19. The spectroscopic analysis device of claim 14, further comprising:

a Raman spectrometer, said Raman spectrometer configured to accept said spectroscopic analysis cell.

* * * * *